United States Patent [19]

Katsumi et al.

[11] 4,440,784

[45] Apr. 3, 1984

[54] ANTI-INFLAMMATORY, ANALGESIC, AND ANTIPYRETIC PHARMACEUTICAL COMPOSITION

[75] Inventors: Ikuo Katsumi, Kobe; Hideo Kondo, Takasago; Katsuji Yamashita; Takayoshi Hidaka, both of Kobe; Kazunori Hosoe, Takasago; Yutaka Ariki, Himeji; Toshiaki Yamashita, Kakogawa; Kiyoshi Watanabe, Akashi, all of Japan

[73] Assignee: Kanegafuchi Chemical Industry Company, Ltd., Osaka, Japan

[21] Appl. No.: 337,130

[22] Filed: Jan. 5, 1982

[30] Foreign Application Priority Data

Feb. 5, 1981 [JP] Japan .................................. 56-16602
Nov. 9, 1981 [JP] Japan .................................. 56-179949

[51] Int. Cl.³ .................... A61K 31/19; A61K 31/235
[52] U.S. Cl. .................................. 424/308; 424/317; 424/324
[58] Field of Search .............................. 424/307, 308

[56] References Cited

U.S. PATENT DOCUMENTS 4,128,664 12/1978 Moore ................................ 424/324

FOREIGN PATENT DOCUMENTS 44-17155 of 1969 Japan .

OTHER PUBLICATIONS

Van Der Goot et al., Eur. Med. Chem., No. 5, pp. 425-428, Sep.-Oct. 1978.

Primary Examiner—Stanley J. Friedman
Attorney, Agent, or Firm—Armstrong, Nikaido, Marmelstein & Kubovcik

[57] ABSTRACT

A new anti-inflammatory, analgesic, and antipyretic pharmaceutical composition is disclosed which contains a 3,5-di-tert-butyl-4-hydroxystyrene derivative of the formula:

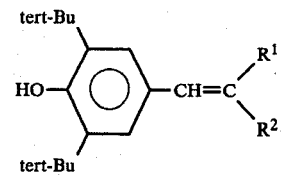

wherein $R^1$ stands for a group represented by $COR^3$ [$R^3$ denotes a group of $OR^4$ ($R^4$ is a hydrogen atom or an alkyl group with $C_1 \sim C_4$), an alkyl group with $C_1 \sim C_3$, a phenyl group, or an amino group], a nitro group, or an alkylsulfonyl group represented by $SO_2R^5$ ($R^5$ is an alkyl group with $C_1 \sim C_3$); and $R^2$ stands for a hydrogen atom, an alkyl group with $C_1 \sim C_4$, a hydroxyalkyl group with $C_1 \sim C_4$, a cyano group, or an acyl group represented by $COR^6$ ($R^6$ is an alkyl group with $C_1 \sim C_3$), or its pharmaceutically acceptable salt as an active ingredient in association with pharmaceutical excipients. The pharmaceutical composition has excellent anti-inflammatory, analgesic, and antipyretic activities and low toxicity.

4 Claims, No Drawings

ANTI-INFLAMMATORY, ANALGESIC, AND ANTIPYRETIC PHARMACEUTICAL COMPOSITION

BRIEF SUMMARY OF THE INVENTION

The present invention relates to a novel anti-inflammatory, analgesic, and antipyretic pharmaceutical composition. More specifically, the present invention relates to an anti-inflammatory, analgesic, and antipyretic pharmaceutical composition which comprises a 3,5-di-tert-butyl-4-hydroxystyrene derivative represented by the general formula (1):

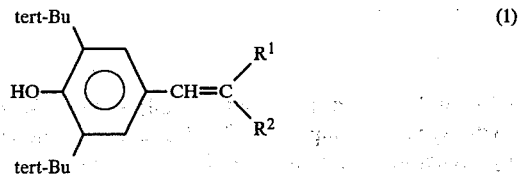

wherein $R^1$ stands for a group represented by $COR^3$ [$R^3$ denotes a group of $OR^4$ ($R^4$ is a hydrogen atom or an alkyl group with $C_1 \sim C_4$), an alkyl group with $C_1 \sim C_3$, a phenyl group, or an amino group], a nitro group, or an alkylsulfonyl group represented by $SO_2R^5$ ($R^5$ is an alkyl group with $C_1 \sim C_3$); and $R^2$ stands for a hydrogen atom, an alkyl group with $C_1 \sim C_4$, a hydroxyalkyl group with $C_1 \sim C_4$, a cyano group, or an acyl group represeted by $COR^6$ ($R^6$ is an alkyl group with $C_1 \sim C_3$), or its pharmaceutically acceptable salt as an active ingredient in association with pharmaceutical excipients.

Inflammation is one of the commonest symptoms. Since salicylic acid was used in the treatment of inflammatory disorders, a vast number of compounds, obtained by synthesis or by extraction from natural sources, have been in use for the treatment. These compounds, however, have each merits and demerits; in general, the medicaments having a potent anti-inflammatory activity tend to be highly toxic, whereas those having low toxicity tend to have a relatively low anti-inflammatory activity. Thus, an anti-inflammatory medicament meeting these two requirements has yet to be found.

The present inventors have made assiduous investigations to develop an anti-inflammatory, analgesic, and antipyretic agent having a potent anti-inflammatory activity and low toxicity. As a result, the present inventors have completed the present invention based on the findings that a 3,5-di-tert-butyl-4-hydroxystyrene derivative represented by the foregoing general formula (1) has excellent anti-inflammatory, analgesic, and antipyretic activities and low toxicity.

DETAILED DESCRIPTION

The following compounds can be cited as specific examples of the compounds represented by the foregoing formula (1):

β-Carboxy-β-(2-hydroxyethyl)-3,5-di-tert-butyl-4-hydroxystyrene (hereinafter referred to as Compound I)

β-Methoxycarbonyl-β-(2-hydroxyethyl)-3,5-di-tert-butyl-4-hydroxystyrene (hereinafter referred to as Compound II)

β-Carboxy-β-ethyl-3,5-di-tert-butyl-4-hydroxystyrene (hereinafter referred to as Compound III)

β-Ethoxycarbonyl-β-acetyl-3,5-di-tert-butyl-4-hydroxystyrene (hereinafter referred to as Compound IV)

β-Acetyl-3,5-di-tert-butyl-4-hydroxystyrene (hereinafter referred to as Compound V)

β-Acetyl-β-methyl-3,5-di-tert-butyl-4-hydroxystyrene (hereinafter referred to as Compound VI)

β-Benzoyl-3,5-di-tert-butyl-4-hydroxystyrene (hereinafter referred to as Compound VII)

β-Carbamoyl-3,5-di-tert-butyl-4-hydroxystyrene (hereinafter referred to as Compound VIII)

β-Carbamoyl-β-cyano-3,5-di-tert-butyl-4-hydroxystyrene (hereinafter referred to as Compound IX)

β-Nitro-3,5-di-tert-butyl-4-hydroxystyrene (hereinafter referred to as Compound X)

β-Methylsulfonyl-β-cyano-3,5-di-tert-butyl-4-hydroxystyrene (hereinafter referred to as Compound XI)

The foregoing compounds represented by the general formula (1) can form salts with bases; as the base, any ones which can form salts with the compounds (1) can optionally be chosen. Specific examples of such salts include, for example, (i) metal salts, especially those with alkali metals, alkaline earth metals, and aluminum, (ii) ammonium salts, and (iii) salts with amines, especially those with methylamine, ethylamine, diethylamine, triethylamine, pyrrolidine, piperidine, morpholine, hexamethyleneimine, aniline, pyridine and so forth. The salts used as an anti-inflammatory, analgesic, and antipyretic agent of the present invention are physiologically acceptable ones which can be chosen, for example, from among the foregoing salts.

The foregoing compounds (1) and their pharmaceutically acceptable salts, having all excellent anti-inflammatory, analgesic, and antipyretic activities and yet low toxicity, can be said to be suitable for the object of the present invention. The foregoing compounds can be synthesized by the following methods:

(1) The desired compound can be synthesized by reacting 3,5-di-tert-butyl-4-hydroxybenzaldehyde with an ylide compound represented by the general formula:

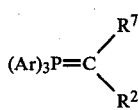

wherein Ar stands for an aryl group; $R^7$ stands for a group of $COR^8$ [$R^8$ denotes an alkoxyl group of $OR^9$ ($R^9$ is an alkyl group with $C_1 \sim C_4$), an alkyl group with $C_1 \sim C_3$, a phenyl group, or an amino group], a nitro group, or an alkylsulfonyl group of $SO_2R^5$ ($R^5$ is the same as defined above); $R^2$ stands for a hydrogen atom, an alkyl group with $C_1 \sim C_4$, a hydroxyalkyl group with $C_1 \sim C_4$, a cyano group, or an acyl group of $COR^6$ ($R^6$ is the same as defined above); further, $R^7$ and $R^2$ may be combined to stand for

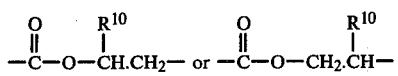

($R^{10}$ is a hydrogen atom or an alkyl group with $C_1 \sim C_2$), forming a ring with $=C<$, according to a method of O. Ister et al. [Helv. Chim. Acta., 40, 1242 (1957)], and, if necessary, further hydrolyzing an ester or amide group in the product obtained above with a suitable acid or base. This method utilizes the so-called Wittig reaction; as an ylide compound to be reacted with the foregoing benzaldehyde derivative, ylide compounds derived from a trialkylphosphine, trialkylphosphite, or triarylarsine, besides the foregoing ylide compound, can also be used in the same manner. Acids or bases to be employed for hydrolysis of an ester or amide group in the compounds obtained include sulfuric acid, p-toluenesulfonic acid, trifluoroacetic acid, sodium hydroxide, potassium hydroxide, barium hydroxide, pyrrolidine, and so forth.

(2) Of the compounds represented by the general formula (1), those represented by the general formula (2):

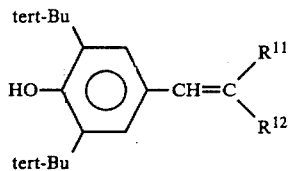

wherein $R^{11}$ stands for a group of $COR^{13}$ [$R^{13}$ denotes $OR^{14}$ ($R^{14}$ is an alkyl group with $C_1 \sim C_4$) or an amino group], a nitro gorup, or an alkylsulfonyl group of $SO_2R^5$ ($R^5$ is the same as defined above); and $R^{12}$ stands for a hydrogen atom, a cyano group, or a group of $COR^6$ ($R^6$ is the same as defined above),
can be synthesized also in the following manner:

They are synthesized by reacting 3,5-di-tert-butyl-4-hydroxybenzaldehyde with a compound represented by the following formula:

wherein $R^{11}$ stands for a group of $COR^{13}$ [$R^{13}$ denotes $OR^{14}$ ($R^{14}$ is an alkyl group with $C_1 \sim C_4$) or an amino group], a nitro group, or an alkylsulfonyl group of $SO_2R^5$ ($R^5$ is the same as defined above); and $R^{15}$ stands for a hydrogen atom, a cyano group, or a group of $COR^{16}$ ($R^{16}$ is a hydroxyl group or an alkyl group with $C_1 \sim C_3$), in the presence of a base or its salt as a catalyst. This reaction utilizes a method known as the Knoevenagel reaction; bases used as a catalyst include ammonia, and a primary or secondary amine, specific examples of the bases and salts thereof being piperidine, pyrrolidine, ammonium acetate, piperidinium acetate, and so on.

When malonic acid monoamide, etc. is used as the foregoing compound represented by the formula of $R^{11}$—$CH_2$—$R^{15}$, decarboxylation takes place in some cases to produce the compound (2) wherein $R^{12}$ is a hydrogen atom.

(3) Of the compounds represented by the general formula (1), those represented by the general formula (3);

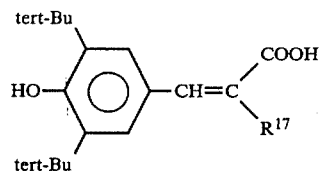

wherein $R^{17}$ stands for an alkyl group with $C_1 \sim C_4$, can be synthesized by subjecting 3,5-di-tert-butyl-4-hydroxybenzaldehyde, an acid anhydride represented by the formula of $(R^{17}CH_2CO)_2O$ ($R^{17}$ is an alkyl group with $C_1 \sim C_4$), and an alkali metal salt of an organic acid represented by the formula of $R^{17}CH_2COOM$ ($R^{17}$ is an alkyl group with $C_1 \sim C_4$ and M is an alkali metal) to the Perkin reaction. Alkali metals which can be used in the reaction include sodium and so forth.

(4) Of the compounds represented by the general formula (1), those represented by the general formula (4):

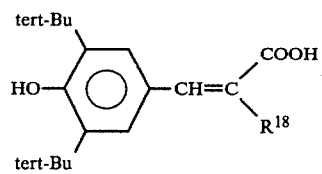

wherein $R^{18}$ stands for an alkyl group with $C_1 \sim C_4$ or a hydroxyalkyl group with $C_1 \sim C_4$, can be synthesized by reacting 3,5-di-tert-butyl-4-hydroxybenzaldehyde with a malonic acid derivative represented by the formula of $R^{18}$—$CH(COOH)_2$ ($R^{18}$ is an alkyl group with $C_1 \sim C_4$ or a hydroxyalkyl group with $C_1 \sim C_4$) in a solvent such as pyridine in the presence of a base such as piperidine, pyrrolidine, and so forth.

Anti-inflammatory, analgesic, and antipyretic agents

The foregoing compounds represented by the general formula (1) and pharmaceutically acceptable salts thereof are useful as anti-inflammatory, analgesic, and anti-pyretic agents. These compounds possess excellent pharmacological activities and low toxicity, as shown in the following experiments.

Anti-inflammatory activity (1) An acute anti-inflammatory activity was evaluated by the method of carrageenan-induced paw edema in rats [C. A. Winter et al., Proc. Soc. Exp. Biol. & Med., 111, 544 (1962)]. Six male Wistar strain rats weighing 150~180 g were used in each group. Test compounds suspended in 2.5% acacia were administered p.o. to rats 1 hour before s.c. injection of 0.1 ml of 1% carrageenan in 0.9% NaCl into one hind paw. The volume of each paw edema was measured 3 and 5 hours after the injection of carrageenan. Percent edema inhibition was calculated by the following equation.

$$\text{Inhibition (\%)} = \left(1 - \frac{\text{Mean swelling volume of foot in the test group}}{\text{Mean swelling volume of foot in the control group}}\right) \times 100$$

The results are shown in Table 1.

TABLE 1

| Compound | | Dose (mg/kg) | Inhibition (%) 3 hours | 5 hours |
|---|---|---|---|---|
| Compound | I | 50 | 44.6 | 41.6 |
| | II | 50 | 52.1 | 41.7 |
| | III | 50 | 12.1 | 18.3 |
| | IV | 50 | 30.3 | 28.4 |
| | V | 50 | 43.2 | 50.0 |
| | VI | 50 | 32.5 | 20.7 |
| | VII | 50 | 16.9 | 19.7 |
| | VIII | 50 | 17.6 | 14.6 |
| | IX | 50 | 40.8 | 34.2 |
| | X | 50 | 11.0 | 17.3 |
| | XI | 50 | 35.1 | 18.3 |

TABLE 1-continued

| Compound | Dose (mg/kg) | Inhibition (%) 3 hours | Inhibition (%) 5 hours |
|---|---|---|---|
| Indomethacin (Known compound) | 5 | 32.8 | 39.2 |
| Phenylbutazone (Known compound) | 100 | 23.6 | 28.9 |

(2) A sub-chronic anti-inflammatory activity was evaluated by the method of paper disk-induced granuloma in rats [Y. Hara et al., Folia Pharmacol. Japon., 73, 557 (1977)]. Six male Wistar strain rats weighing 150~180 g were used in each group. Each paper disk (29±1 mg) was implanted s.c. into the bilateral area of the scapula of rats under anesthesia with amobarbital sodium. Test compounds suspended in 2.5% acacia were administered p.o. once daily for 7 days, starting on the day of surgery (day 0). The rats were killed on day 7, at which time the paper disks with surrounding granulomatous tissues were removed and dried to constant weight overnight, and weighed. Percent inhibition was calculated by the following equation.

$$\text{Inhibition (\%)} = \left(1 - \frac{\text{Mean dried granuloma weight in the test group}}{\text{Mean dried granuloma weight in the control group}}\right) \times 100$$

The results are shown in Table 2.

TABLE 2

| Compound | Dose (mg/kg/day) | Inhibition (%) |
|---|---|---|
| Compound V | 25 | 29.4 |
|  | 100 | 29.0 |
| IX | 25 | 27.0 |
|  | 100 | 25.0 |
| Phenylbutazone (Known compound) | 25 | 5.6 |
|  | 100 | 24.2 |
| Indomethacin (Known compound) | 1.25 | 14.0 |
|  | 5 | 25.5 |

(3) A chronic anti-inflammatory activity was evaluated by the method of adjuvant-induced arthritis in rats [D. T. Walz et al., J. Pharmacol. and Exp. Ther., 178, 223 (1971)]. Eight male Sprague-Dawley strain rats weighing 190~230 g were used in each group. Into the left hind paw of rats was injected i.d. 0.5 mg of Mycobacterium butyricum suspended in 0.05 ml of paraffin oil. Test compounds suspended in 2.5% acacia were administered p.o. once daily for 21 days, starting on the day of the injection of an adjuvant (day 0). Paw volumes of adjuvant-injected and uninjected feet were measured on day 14 and on day 21. Percent inhibition was calculated by the following equation.

$$\text{Inhibition (\%)} = \left(1 - \frac{\text{Mean swelling volume of foot in the test group}}{\text{Mean swelling volume of foot in the control group}}\right) \times 100$$

The results are shown in Table 3.

TABLE 3

| Compound | Dose (mg/kg/day) | Inhibition (%) Injected foot Day 14 | Inhibition (%) Injected foot Day 21 | Inhibition (%) Uninjected foot Day 14 | Inhibition (%) Uninjected foot Day 21 |
|---|---|---|---|---|---|
| Compound V | 12.5 | 12.0 | 29.6 | 10.6 | 14.7 |
|  | 50 | 37.3 | 58.8 | 74.5 | 69.3 |
| IX | 12.5 | 33.3 | 46.1 | 70.3 | 42.6 |
|  | 50 | 31.6 | 29.6 | 40.5 | 42.6 |
| Ibuprofen (Known compound) | 12.5 | −2.6 | −17.4 | 13.5 | −7.4 |
|  | 50 | −1.7 | 28.7 | 32.4 | 44.4 |

Analgesic activity

An analgesic activity was evaluated by the method of acetic acid-induced writhing in mice [R. Koster et al., Federation Proc., 18, 412 (1959)]. Ten male ddY strain mice weighing 20~25 g were used in each group. Test compounds suspended in 2.5% acacia were administered p.o. to the mice. One hour later, the mice were injected i.p. with 0.6% acetic acid in a volume of 0.1 ml/10 g body weight. The number of writhes in each of mice was counted for 20 minutes after the injection of the acetic acid. Percent inhibition was calculated by the following equation.

$$\text{Inhibition (\%)} = \left(1 - \frac{\text{Mean number of writhes in the test group}}{\text{Mean number of writhes in the control group}}\right) \times 100$$

The results are shown in Table 4.

TABLE 4

| Compound | Dose (mg/kg) | Inhibition (%) |
|---|---|---|
| Compound I | 100 | 74.5 |
| II | 100 | 79.8 |
| III | 100 | 28.2 |
| IV | 100 | 56.9 |
| V | 100 | 53.1 |
| VI | 100 | 47.8 |
| VII | 100 | 33.0 |
| VIII | 100 | 25.8 |
| IX | 100 | 50.7 |
| X | 100 | 24.4 |
| XI | 50 | 31.6 |
| Indomethacin (Known compound) | 5 | 62.7 |
| Aspirin (Known compound) | 100 | 38.0 |

Antipyretic activity

An antipyretic activity was evaluated by the method of yeast-induced fever in rats [Y. Yanagi et al., Folia Pharmacol. Japon., 74, 735 (1978)]. Five male Wistar strain rats weighing 150~180 g were used in each group. A 20% Baker's yeast suspension in 0.9% NaCl was injected s.c. into the dorsal region of rats in a volume of 1 ml/100 g body weight. Test compounds suspended in 2.5% acacia were administered p.o. to rats with a rectal temperature of over 38.6° C., 18 hours after the injection of the yeast. The rectal temperature was determined with a thermometer, 1, 3 and 5 hours after the administration of test compounds. Percent inhibition was calculated by the following equation.

Inhibition (%) =

-continued $$\left(1 - \frac{\text{Mean increase in rectal temperature in the test group}}{\text{Mean increase in rectal temperature in the control group}}\right) \times 100$$

The results are shown in Table. 5.

TABLE 5

| Compound | Dose (mg/kg) | Inhibition (%) | | |
|---|---|---|---|---|
| | | 1 hour | 3 hours | 5 hours |
| Compound I | 100 | 53.1 | 98.9 | 70.3 |
| II | 100 | 42.5 | 64.5 | 59.7 |
| III | 100 | 14.6 | 31.8 | 19.5 |
| IV | 100 | 23.0 | 40.9 | 41.6 |
| V | 100 | 34.5 | 70.9 | 64.9 |
| VI | 100 | 38.1 | 45.5 | 41.6 |
| VII | 100 | 15.9 | 27.7 | 21.4 |
| VIII | 100 | 19.9 | 25.9 | 16.9 |
| IX | 100 | 35.4 | 77.3 | 87.0 |
| X | 100 | 18.6 | 30.5 | 23.4 |
| XI | 50 | 23.2 | 31.2 | 19.9 |
| Indomethacin (Known compound) | 5 | 35.4 | 56.4 | 66.2 |

Toxicity

Female ICR strain mice weighing 20~25 g in groups of six each were used for toxicity tests. Test compounds suspended in 2.5% acacia were administered p.o. to the mice. The animals were observed daily for 14 days after the administration. The $LD_{50}$ values were estimated from mortality (No. of dead mice/No. of mice used).

The results are shown in Table 6.

TABLE 6

| Compound | $LD_{50}$ (mg/kg) |
|---|---|
| Compound I | >1000 |
| II | >1000 |
| III | >1000 |
| IV | >1000 |
| V | >1000 |
| VI | >1000 |
| VII | >1000 |
| VIII | >1000 |
| IX | >1000 |
| X | >1000 |
| XI | 250–500 |

Moreover, the compounds (1) showed only small gastro-intestinal damages in rats.

Preparations and dosage

The compounds represented by the general formula (1) and their pharmaceutically acceptable salts can be used as an anti-inflammatory, analgesic, and antipyretic agent in humans. For these purposes, the compounds can be administered orally, rectally, topically, or parenterally in a pharmaceutical dosage form, for example, tablets, capsules, granules, suppositories, ointments, syrups, injections and the like. These pharmaceutical dosage forms comprise the compounds (1) or their pharmaceutically acceptable salts as an active ingredient in association with pharmaceutical excipients, e.g., pharmaceutically acceptable organic or inorganic substances in either solid or liquid form, for example, crystalline cellulose, gelatin, lactose, starch, magnesium stearate, polyalkylene glycol, talc, fat, gum, and the like. The content of the compounds (1) or their pharmaceutically acceptable salts in such compositions or preparations may be varied between 0.2 and 100% by weight. Furthermore, such compositions or preparations may contain other compatible pharmaceutical agents including anti-inflammatory, analgesic, or antipyretic agents.

The pharmaceutical compositions or preparations are prepared so that a dosage unit contains between one and 5000 mg, preferably between three and 1000 mg of the active ingredient. The compounds (1) and their pharmaceutically acceptable salts may be administered in a single dose, or preferably in divided doses. The dosage range of the pharmaceutical compositions or preparations containing the compounds (1) or their pharmaceutically acceptable salts is from about 10 to about 1000 mg per man per day, preferably from about 20 to about 5000 mg per man per day, based on the active ingredient.

REFERENCE EXAMPLE 1

Synthesis of Compound I

In 150 ml of dimethyl sulfoxide (DMSO) were dissolved 18 g of 3,5-di-tert-butyl-4-hydroxybenzaldehyde and 27 g of α-triphenylphosphoranylidene-γ-butyrolactone, and the reaction was carried out at 80° C. on a hot water bath with stirring for 20 hours. After the completion of the reaction, 800 ml of chloroform was added to the cooled reaction mixture, and the resulting mixture washed 5 times with the same volume of water to remove the solvent DMSO. The chloroform layer was separated and concentrated to dryness under reduced pressure to remove the chloroform. The residue was crystallized by addition of ethanol and further recrystallized from ethanol to afford 18 g of α-(3,5-di-tert-butyl-4-hydroxybenzylidene)-γ-butyrolactone. To 100 ml of aqueous 1 N sodium hydroxide was added 1.5 g of α-(3,5-di-tert-butyl-4-hydroxybenzylidene)-γ-butyrolactone, and the hydrolysis reaction was carried out at 90°~100° C. in an oil bath with stirring in an atmosphere of nitrogen for one hour. After the completion of the reaction, 10% of sulfuric acid was added gradually to the cooled reaction mixture for acidification, whereupon precipitates were formed. The precipitates were collected by filtration and washed sufficiently with water. The precipitates were dissolved in benzene to effect crystallization, affording 1.0 g of the desired Compound I.

REFERENCE EXAMPLE 2

Synthesis of Compound VI

In 20 ml of DMSO were placed 2.3 g of 3,5-di-tert-butyl-4-hydroxybenzaldehyde and 4.5 g of 3-triphenylphosphoranylidene-2-butanone, and the reaction was carried out at 80° C. on a hot water bath with stirring for 40 hours. After the completion of the reaction, 200 ml of chloroform was added to the cooled reaction mixture, and the resulting mixture washed 10 times with the same volume of water to remove the solvent DMSO. The chloroform layer was separated and the chloroform removed under reduced pressure. The residue was dissolved in an aqueous alcohol (alcohol/water=7/3) to effect crystallization. Then, the crystals obtained were dissolved in acetone, and n-hexane was added to the solution to separate crystals again.

Yield: 2.0 g.

REFERENCE EXAMPLE 3

Synthesis of Compound IX

To 30 ml of ethanol were added 3.5 g of 3,5-di-tert-butyl-4-hydroxybenzaldehyde, 1.3 of cyano-acetamide, and 1 ml of piperidine. The mixture was stirred at 40°~50° C., whereby the mixture became uniform after a while. The solution was further stirred at that temperature for 4 hours to complete the reaction. After the completion of the reaction, the solvent was removed under reduced pressure, then the residue dissolved in chloroform and washed 3 times with dilute hydrochloric acid. The chloroform layer was separated and the chloroform removed under reduced pressure. The residue was dissolved in ethanol to effect crystallization.

Yield: 3.5 g.

EXAMPLE 1

A mixture of 100 g of Compound I, 55 g of lactose, and 41 g of dried potato starch was kneaded with 20 ml of water. The kneaded mixture was then pressed out through a 16 mesh screen, then dried at 40° C. to form granules. The granules were mixed uniformly with 4 g of magnesium stearate and then compressed into tablets (200 mg each) containing each 100 mg of Compound I according to an ordinary method.

EXAMPLE 2

Compound IX was used in place of Compound I and tablets (200 mg each) containing each 100 mg of Compound IX were prepared in the same manner as in Example 1.

EXAMPLE 3

After 196 g of granules obtained in the same manner as Example 1 had been mixed uniformly with 4 g of magnesium stearate, the mixture was sealed in No. 2 hard capsules (200 mg each) to provide hard capsules containing each 100 mg of Compound I.

EXAMPLE 4

Compound IX was used in place of Compound I and hard capsules containing each 100 mg of Compound IX were prepared in the same manner as in Example 3.

EXAMPLE 5

Compound I: 10.0 g,
lactose: 85.0 g,
crystalline cellulose: 4.5 g,
magnesium stearate: 0.5 g.

The components described above were mixed sufficiently to prepare powders containing 100 mg of Compound I in each 1 g thereof.

EXAMPLE 6

Compound IX was used in place of Compound I and powders containing 100 mg of Compound IX in each 1 g thereof were prepared in the same manner as in Example 5.

What is claimed is:

1. An anti-inflammatory, analgesic, and antipyretic pharmaceutical composition which comprises an effective amount of a 3,5-di-tert-butyl-4-hydroxystyrene derivative represented by the general formula:

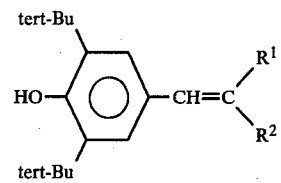

wherein $R^1$ stands for a group represented by —$COOR^4$; $R^4$ is a hydrogen atom or an alkyl group with $C_1 \sim C_4$; $R^2$ stands for an alkyl group with $C_1 \sim C_4$, a hydroxyalkyl group with $C_1 \sim C_4$, or an acyl group represented by —$COR^6$; and $R^6$ is an alkyl group with $C_1 \sim C_3$ or its pharmaceutically acceptable salt as an active ingredient in combination with pharmaceutical excipients.

2. The anti-inflammatory, analgesic, and antipyretic pharmaceutical composition according to claim 1 wherein the derivative (1) is a compound represented by the formula:

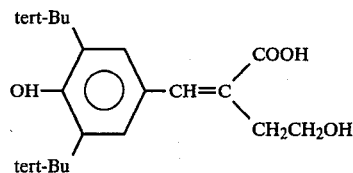

3. The anti-inflammatory, analgesic, and antipyretic pharmaceutical composition according to claim 1 or claim 2 wherein the derivative (1) is a compound represented by the formula:

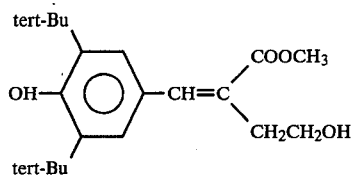

4. The anti-inflammatory, analgesic, and antipyretic pharmaceutical composition according to claim 1 or claim 2 wherein the derivative (1) is a compound represented by the formula:

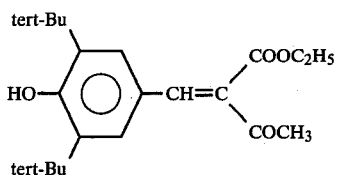

* * * * *